United States Patent
Zones (12)

(10) Patent No.: US 6,881,323 B2
(45) Date of Patent: *Apr. 19, 2005

(54) HYDROCARBON CONVERSION USING ZEOLITE SSZ-54

(75) Inventor: Stacey Zones, San Francisco, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 321 days.

This patent is subject to a terminal disclaimer.

(21) Appl. No.: 10/186,883

(22) Filed: Jun. 28, 2002

(65) Prior Publication Data

US 2004/0004026 A1 Jan. 8, 2004

(51) Int. Cl.⁷ .................. C10G 11/00; C10G 35/04; C07C 15/67; C07C 2/64; C07C 2/04
(52) U.S. Cl. .................. 208/113; 208/134; 208/137; 585/407; 585/446; 585/510; 585/643; 585/648
(58) Field of Search ................. 208/113, 134, 208/137; 585/407, 446, 510, 643, 648

(56) References Cited

U.S. PATENT DOCUMENTS 6,475,463 B1 * 11/2002 Elomari et al. ............. 423/706
6,676,923 B1 * 1/2004 Zones et al. ................ 423/718

OTHER PUBLICATIONS

U.S. Appl. No. 10/187,136, filed Jun. 28, 2002, Reynolds.

Szostak, Handbook of Molecular Sieves, Van Nostrand Reinhold, 1992, pp. 538–542.

* cited by examiner

Primary Examiner—Walter D. Griffin
Assistant Examiner—Tam M. Nguyen
(74) Attorney, Agent, or Firm—Richard J. Sheridan

(57) ABSTRACT

The present invention relates to new crystalline zeolite SSZ-54 prepared using a templating agent comprising N-isopropyl ethylenediamine, or a mixture of 1-N-isopropyl diethylenetriamine and isobutylamine, and processes employing SSZ-54 in a catalyst.

34 Claims, 4 Drawing Sheets

HYDROCARBON CONVERSION USING ZEOLITE SSZ-54

BACKGROUND OF THE INVENTION

1. Field of the Invention

The present invention relates to new crystalline zeolite SSZ-54, a method for preparing SSZ-54 using a templating agent comprising N-isopropyl ethylenediamine, or a mixture of 1-N-isopropyl diethylenetriamine and isobutylamine, and processes employing SSZ-54 in a catalyst.

2. State of the Art

Because of their unique sieving characteristics, as well as their catalytic properties, crystalline molecular sieves and zeolites are especially useful in applications such as hydrocarbon conversion, gas drying and separation. Although many different crystalline molecular sieves have been disclosed, there is a continuing need for new zeolites with desirable properties for gas separation and drying, hydrocarbon and chemical conversions, and other applications. New zeolites may contain novel internal pore architectures, providing enhanced selectivities in these processes.

Crystalline aluminosilicates are usually prepared from aqueous reaction mixtures containing alkali or alkaline earth metal oxides, silica, and alumina. Crystalline borosilicates are usually prepared under similar reaction conditions except that boron is used in place of aluminum. By varying the synthesis conditions and the composition of the reaction mixture, different zeolites can often be formed.

SUMMARY OF THE INVENTION

The present invention provides a process for converting hydrocarbons comprising contacting a hydrocarbonaceous feed at hydrocarbon converting conditions with a catalyst comprising a zeolite having a mole ratio greater than about 20 of an oxide of a first tetravalent element to an oxide of a second tetravalent element which is different from said first tetravalent element, trivalent element, pentavalent element or mixture thereof and having, after calcination, the X-ray diffraction pattern of FIG. 1. The zeolite may be predominantly in the hydrogen form. It may also be substantially free of acidity.

Further provided by the present invention is a hydrocracking process comprising contacting a hydrocarbon feedstock under hydrocracking conditions with a catalyst comprising the zeolite of this invention, preferably predominantly in the hydrogen form.

Also included in this invention is a process for increasing the octane of a hydrocarbon feedstock to produce a product having an increased aromatics content comprising contacting a hydrocarbonaceous feedstock which comprises normal and slightly branched hydrocarbons having a boiling range above about 40° C. and less than about 200° C., under aromatic conversion conditions with a catalyst comprising the zeolite of this invention made substantially free of acidity by neutralizing said zeolite with a basic metal. Also provided in this invention is such a process wherein the zeolite contains a Group VIII metal component.

Also provided by the present invention is a catalytic cracking process comprising contacting a hydrocarbon feedstock in a reaction zone under catalytic cracking conditions in the absence of added hydrogen with a catalyst comprising the zeolite of this invention, preferably predominantly in the hydrogen form. Also included in this invention is such a catalytic cracking process wherein the catalyst additionally comprises a large pore crystalline cracking component.

This invention further provides an isomerization process for isomerizing $C_4$ to $C_7$ hydrocarbons, comprising contacting a feed having normal and slightly branched $C_4$ to $C_7$ hydrocarbons under isomerizing conditions with a catalyst comprising the zeolite of this invention, preferably predominantly in the hydrogen form. The zeolite may be impregnated with at least one Group VIII metal, preferably platinum. The catalyst may be calcined in a steam/air mixture at an elevated temperature after impregnation of the Group VIII metal.

Also provided by the present invention is a process for alkylating an aromatic hydrocarbon which comprises contacting under alkylation conditions at least a molar excess of an aromatic hydrocarbon with a $C_2$ to $C_{20}$ olefin under at least partial liquid phase conditions and in the presence of a catalyst comprising the zeolite of this invention, preferably predominantly in the hydrogen form. The olefin may be a $C_2$ to $C_4$ olefin, and the aromatic hydrocarbon and olefin may be present in a molar ratio of about 4:1 to about 20:1, respectively. The aromatic hydrocarbon may be selected from the group consisting of benzene, toluene, ethylbenzene, xylene, naphthalene, naphthalene derivatives or mixtures thereof.

Further provided in accordance with this invention is a process for transalkylating an aromatic hydrocarbon which comprises contacting under transalkylating conditions an aromatic hydrocarbon with a polyalkyl aromatic hydrocarbon under at least partial liquid phase conditions and in the presence of a catalyst comprising the zeolite of this invention, preferably predominantly in the hydrogen form. The aromatic hydrocarbon and the polyalkyl aromatic hydrocarbon may be present in a molar ratio of from about 1:1 to about 25:1, respectively.

The aromatic hydrocarbon may be selected from the group consisting of benzene, toluene, ethylbenzene, xylene, or mixtures thereof, and the polyalkyl aromatic hydrocarbon may be a dialkylbenzene.

Further provided by this invention is a process to convert paraffins to aromatics which comprises contacting paraffins under conditions which cause paraffins to convert to aromatics with a catalyst comprising the zeolite of this invention, said catalyst comprising gallium, zinc, or a compound of gallium or zinc.

In accordance with this invention there is also provided a process for isomerizing olefins comprising contacting said olefin under conditions which cause isomerization of the olefin with a catalyst comprising the zeolite of this invention.

Further provided in accordance with this invention is a process for isomerizing an isomerization feed comprising an aromatic $C_8$ stream of xylene isomers or mixtures of xylene isomers and ethylbenzene, wherein a more nearly equilibrium ratio of ortho-, meta- and para-xylenes is obtained, said process comprising contacting said feed under isomerization conditions with a catalyst comprising the zeolite of this invention.

The present invention further provides a process for oligomerizing olefins comprising contacting an olefin feed under oligomerization conditions with a catalyst comprising the zeolite of this invention.

The present invention further provides a process for the production of higher molecular weight hydrocarbons from lower molecular weight hydrocarbons comprising the steps of:

(a) introducing into a reaction zone a lower molecular weight hydrocarbon-containing gas and contacting said gas in said zone under $C_{2+}$ hydrocarbon synthesis conditions with SSZ-54 and a metal or metal compound capable of converting the lower molecular weight hydrocarbon to a higher molecular weight hydrocarbon; and (b) withdrawing from said reaction zone a higher molecular weight hydrocarbon-containing stream.

The metal or metal compound can comprise a lanthanide or actinide metal or metal compound, and the lower molecular weight hydrocarbon can be methane.

Further provided by the present invention is a process for converting lower alcohols and other oxygenated hydrocarbons comprising contacting said lower alcohol or other oxygenated hydrocarbon under conditions to produce liquid products with a catalyst comprising a zeolite having a mole ratio greater than about 20 of an oxide of a first tetravalent element to an oxide of a second tetravalent element which is different from said first tetravalent element, trivalent element, pentavalent element or mixture thereof and having, after calcination, the X-ray diffraction pattern of FIG. 1.

DETAILED DESCRIPTION OF THE INVENTION

The present invention comprises a family of crystalline, medium pore zeolites designated herein "zeolite SSZ-54" or simply "SSZ-54". As used herein, the term "medium pore" means having an average pore size diameter greater than about 4.5–6 Angstroms.

Figure 1:
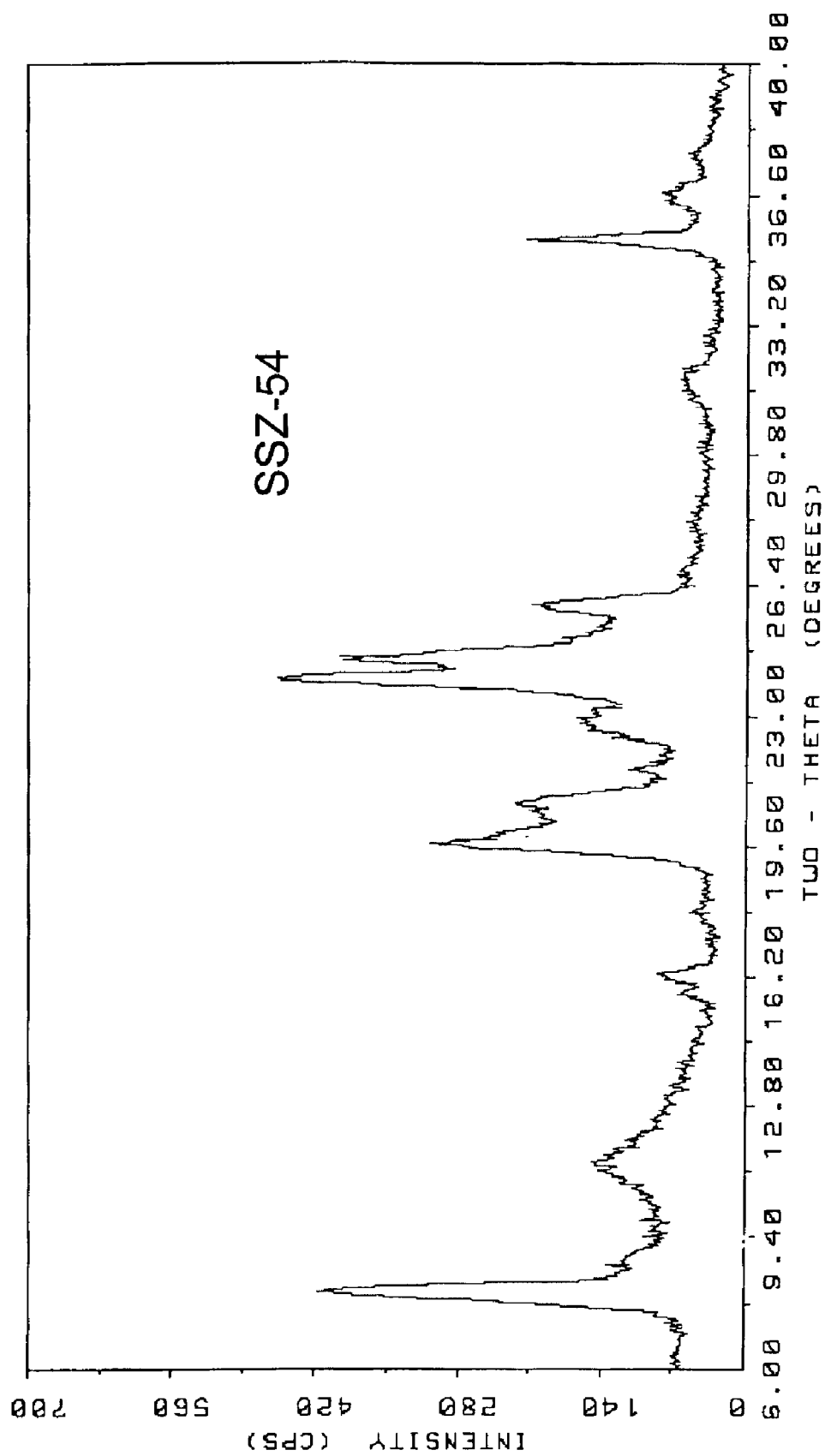
FIG. 1 is an X-ray diffraction pattern of a calcined sample of SSZ-54.
Figure 2:
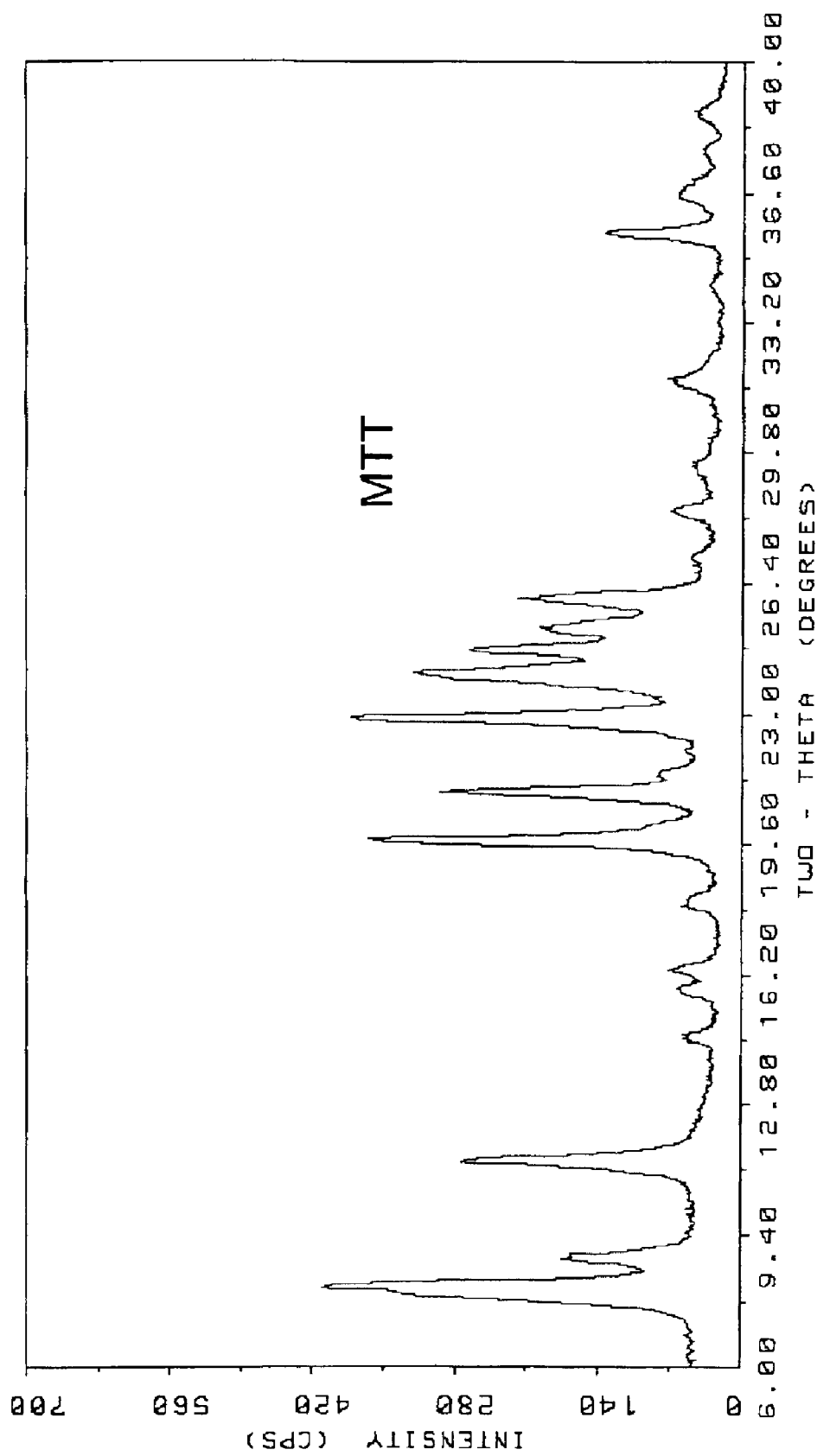
FIG. 2 is an X-ray diffraction pattern of a calcined sample of a zeolite having the MTT crystal structure.
Figure 3:
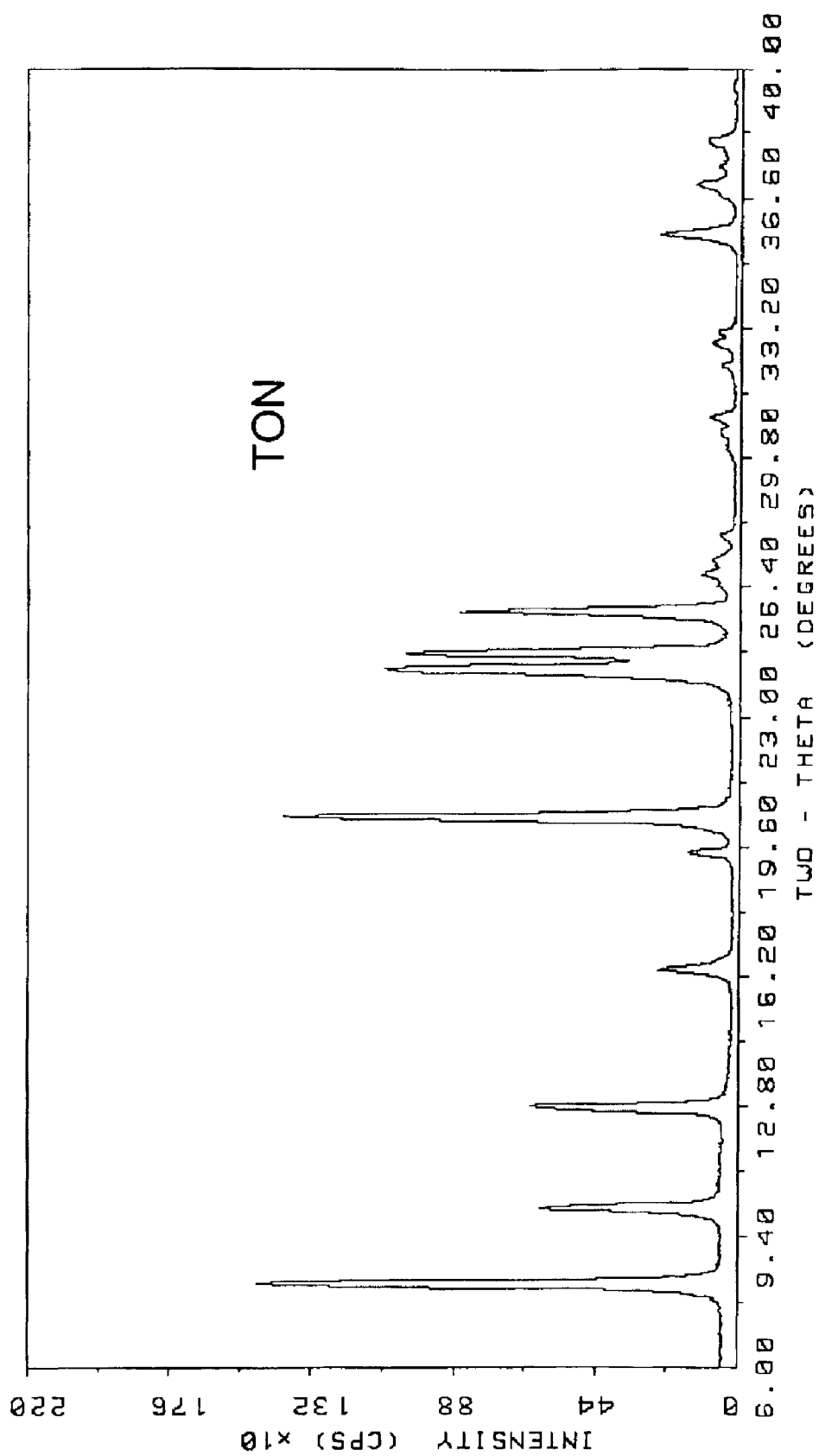
FIG. 3 is an X-ray diffraction pattern of a calcined sample of a zeolite having the TON crystal structure.

While not wishing to be bound by any particular theory, it is believed that SSZ-54 is an intergrowth of the MTT and TON crystal structures. FIG. 1 shows the X-ray diffraction pattern of a calcined sample of SSZ-54. FIG. 2 shows the X-ray diffraction pattern of a calcined sample of a pure phase zeolite having the MTT crystal structure, and FIG. 3 shows the X-ray diffraction pattern of a calcined sample of a pure phase zeolite having the TON crystal structure. It can be seen that there are similarities between the pattern for SSZ-54 and the patterns for MTT and TON.

Figure 4:
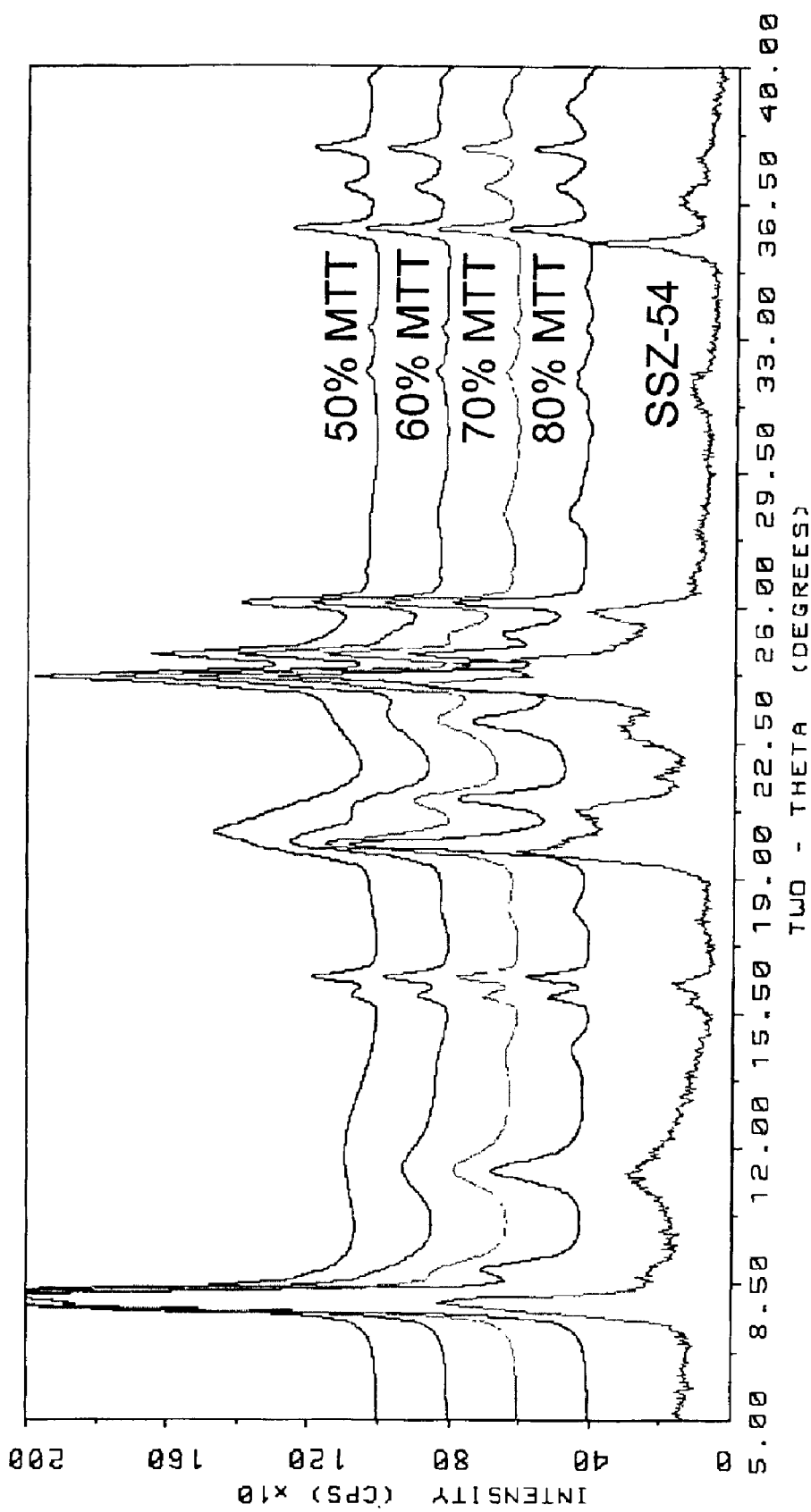
FIG. 4 shows calculated X-ray patterns of calcined zeolites having about 50%, 60%, 70% or 80% MTT crystal structure and the balance the TON crystal structure. For comparison purposes, FIG. 4 also shows the X-ray diffraction pattern for SSZ-54.

FIG. 4 shows calculated X-ray diffraction patterns for zeolites that are an intergrowth of the MTT and TON crystal structures. The calculated patterns are for intergrowths containing about 50%, 60%, 70% and 80% MTT and about 50%, 40%, 30% and 20% TON, respectively. FIG. 4 also shows the X-ray diffraction pattern for SSZ-54. It can be seen that there is a reasonably good correlation between the calculated pattern of 70% MTT/30% TON and the SSZ-54 pattern.

It is further believed that the peak broadening seen in the SSZ-54 pattern of FIG. 4 is due to disorder in the SSZ-54 crystal structure rather than exclusively to small crystal size. This is further evidence that SSZ-54 is an intergrowth of more than one crystal structure.

When needle-like crystals of SSZ-54 were examined by TEM, the cross-section showed TON and MTT domains within the same crystal. This is further evidence that SSZ-54 is an intergrowth of TON and MTT crystal structures.

After calcination, the SSZ-54 has a crystalline structure whose X-ray powder diffraction pattern includes the characteristic lines shown in Table I below.

TABLE I

Calcined SSZ-54

| Two Theta (deg.)[a] | Relative Intensity |
|---|---|
| 8.06 | VS |
| 8.78 | W |
| 11.32 | W |
| 15.82 | W |
| 16.28 | W |
| 17.97 | W |
| 19.64 | S–VS |
| 20.68 | VS |
| 22.92 | W–M |
| 24.00 | VS |
| 24.5 | VS |
| 25.94 | M |
| 31.76 | W |
| 35.48 | M |
| 36.62 | W |
| 37.65 | W |

[a] ±0.2
[b] The X-ray patterns provided are based on a relative intensity scale in which the strongest line in the X-ray pattern is assigned a value of 100: W(weak) is less than 20; M(medium) is between 20 and 40; S(strong) is between 40 and 60; VS(very strong) is greater than 60.

Table IA below shows the characteristic X-ray powder diffraction lines for calcined SSZ-54 including actual relative intensities.

TABLE IA

Calcined SSZ-54

| Two Theta (deg.)[a] | Relative Intensity |
|---|---|
| 8.06 | 68 |
| 8.78 | 10 |
| 11.32 | 17 |
| 15.82 | 8 |
| 16.28 | 4 |
| 17.97 | 1 |
| 19.64 | 58 |
| 20.68 | 77 |
| 22.92 | 19 |
| 24.00 | 90 |
| 24.5 | 100 |
| 25.94 | 28 |
| 31.76 | 18 |
| 35.48 | 23 |
| 36.62 | 13 |
| 37.65 | 4 |

In preparing SSZ-54 zeolites, N-isopropyl ethylenediamine, or a mixture of 1-N-isopropyl diethylenetriamine and isobutylamine is used as a crystallization template (sometimes called a structure directing agent). In general, SSZ-54 is prepared by contacting an active source of one or more oxides selected from the group consisting of monovalent element oxides, divalent element oxides, trivalent element oxides, and tetravalent element oxides with the templating agent.

The templating agents of this invention have the following chemical structures:

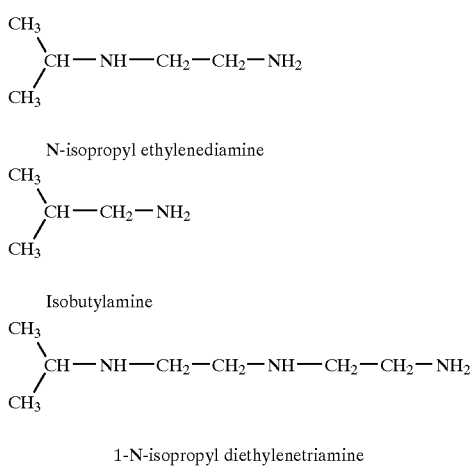

N-isopropyl ethylenediamine

Isobutylamine

1-N-isopropyl diethylenetriamine

When the templating agent is a mixture of 1-N-isopropyl diethylenetriamine and isobutylamine, the mole ratio of 1-N-isopropyl diethylenetriamine to isobutylamine may be about 1:8.

SSZ-54 is prepared from a reaction mixture having the composition shown in Table A below.

TABLE A

| | Reaction Mixture | |
|---|---|---|
| | Typical | Preferred |
| $YO_2/W_aO_b$ | 25–100 | 30–70 |
| $OH^-/YO_2$ | 0.15–0.50 | 0.20–0.30 |
| $Q/YO_2$ | 0.10–1.00 | 0.10–0.40 |
| $M_{2/n}/YO_2$ | 0.03–0.20 | 0.05–0.15 |
| $H_2O/YO_2$ | 10–75 | 15–40 | where Y, W, Q, M and n are as defined above, and a is 1 or 2, and b is 2 when a is 1 (i.e., W is tetravalent) and b is 3 when a is 2 (i.e., W is trivalent).

In practice, SSZ-54 is prepared by a process comprising:
(a) preparing an aqueous solution containing sources of at least one oxide capable of forming a crystalline molecular sieve and the templating agent of this invention;
(b) maintaining the aqueous solution under conditions sufficient to form crystals of SSZ-54; and
(c) recovering the crystals of SSZ-54.

Accordingly, SSZ-54 may comprise the crystalline material and the templating agent in combination with metallic and non-metallic oxides bonded in tetrahedral coordination through shared oxygen atoms to form a cross-linked three dimensional crystal structure. The metallic and non-metallic oxides comprise one or a combination of oxides of a first tetravalent element(s), and one or a combination of a second tetravalent element(s) different from the first tetravalent element(s), trivalent element(s), pentavalent element(s) or mixture thereof. The first tetravalent element(s) is preferably selected from the group consisting of silicon, germanium and combinations thereof. More preferably, the first tetravalent element is silicon. The second tetravalent element (which is different from the first tetravalent element), trivalent element and pentavalent element is preferably selected from the group consisting of aluminum, gallium, iron, boron, titanium, indium, vanadium and combinations thereof. More preferably, the second trivalent or tetravalent element is aluminum or boron.

Typical sources of aluminum oxide for the reaction mixture include aluminates, alumina, aluminum colloids, aluminum oxide coated on silica sol, hydrated alumina gels such as $Al(OH)_3$ and aluminum compounds such as $AlCl_3$ and $Al_2(SO_4)_3$. Typical sources of silicon oxide include silicates, silica hydrogel, silicic acid, fumed silica, colloidal silica, tetra-alkyl orthosilicates, and silica hydroxides. Boron, as well as gallium, germanium, titanium, indium, vanadium and iron, can be added in forms corresponding to their aluminum and silicon counterparts.

A source zeolite reagent may provide a source of aluminum or boron. In most cases, the source zeolite also provides a source of silica. The source zeolite in its dealuminated or deboronated form may also be used as a source of silica, with additional silicon added using, for example, the conventional sources listed above. Use of a source zeolite reagent as a source of alumina for the present process is more completely described in U.S. Pat. No. 5,225,179, issued Jul. 6, 1993 to Nakagawa entitled "Method of Making Molecular Sieves", the disclosure of which is incorporated herein by reference.

Typically, an alkali metal hydroxide and/or an alkaline earth metal hydroxide, such as the hydroxide of sodium, potassium, lithium, cesium, rubidium, calcium, and magnesium, is used in the reaction mixture; however, this component can be omitted so long as the equivalent basicity is maintained. The templating agent may be used to provide hydroxide ion. Thus, it may be beneficial to ion exchange, for example, the halide for hydroxide ion, thereby reducing or eliminating the alkali metal hydroxide quantity required. The alkali metal cation or alkaline earth cation may be part of the as-synthesized crystalline oxide material, in order to balance valence electron charges therein.

The reaction mixture is maintained at an elevated temperature until the crystals of the SSZ-54 zeolite are formed. The hydrothermal crystallization is usually conducted under autogenous pressure, at a temperature between 100° C. and 200° C., preferably between 135° C. and 160° C. The crystallization period is typically greater than 1 day and preferably from about 3 days to about 20 days.

Preferably, the zeolite is prepared using mild stirring or agitation.

During the hydrothermal crystallization step, the SSZ-54 crystals can be allowed to nucleate spontaneously from the reaction mixture. The use of SSZ-54 crystals as seed material can be advantageous in decreasing the time necessary for complete crystallization to occur. In addition, seeding can lead to an increased purity of the product obtained by promoting the nucleation and/or formation of SSZ-54 over any undesired phases. When used as seeds, SSZ-54 crystals are added in an amount between 0.1 and 10% of the weight of silica used in the reaction mixture.

Once the zeolite crystals have formed, the solid product is separated from the reaction mixture by standard mechanical separation techniques such as filtration. The crystals are water-washed and then dried, e.g., at 90° C. to 150° C. for from 8 to 24 hours, to obtain the as-synthesized SSZ-54 zeolite crystals. The drying step can be performed at atmospheric pressure or under vacuum.

SSZ-54 as prepared has a mole ratio of an oxide selected from silicon oxide, germanium oxide and mixtures thereof to an oxide selected from aluminum oxide, gallium oxide, iron oxide, boron oxide, titanium oxide, indium oxide, vanadium oxide and mixtures thereof greater than about 20; and has, after calcination, the X-ray diffraction pattern of FIG. 1. SSZ-54 further has a composition, as synthesized (i.e., prior to removal of the templating agent from the zeolite) and in the anhydrous state, in terms of mole ratios, shown in Table B below.

TABLE B

As-Synthesized SSZ-54

| | |
|---|---|
| $YO_2/W_cO_d$ | 25–100 |
| $M_{2/n}/YO_2$ | 0.02–0.06 |
| $Q/YO_2$ | 0.01–0.04 | where Y, W, c, d, M, n and Q are as defined above.

SSZ-54 can be made essentially aluminum free, i.e., having a silica to alumina mole ratio of ∞. A method of increasing the mole ratio of silica to alumina is by using standard acid leaching or chelating treatments. However, essentially aluminum-free SSZ-54 can be synthesized directly using essentially aluminum-free silicon sources as the main tetrahedral metal oxide component, if boron is also present. SSZ-54 can also be prepared directly as either an aluminosilicate or a borosilicate.

Lower silica to alumina ratios may also be obtained by using methods which insert aluminum into the crystalline framework. For example, aluminum insertion may occur by thermal treatment of the zeolite in combination with an alumina binder or dissolved source of alumina. Such procedures are described in U.S. Pat. No. 4,559,315, issued on Dec. 17, 1985 to Chang et al.

It is believed that SSZ-54 is comprised of a new framework structure or topology which is characterized by its X-ray diffraction pattern. After calcination, the SSZ-54 zeolites have a crystalline structure whose X-ray powder diffraction pattern exhibits the characteristic lines of FIG. 1.

The X-ray powder diffraction patterns were determined by standard techniques. The radiation was the K-alpha/doublet of copper.

Minor variations in the diffraction pattern can result from variations in the silica-to-alumina or silica-to-boron mole ratio of the particular sample due to changes in lattice constants. In addition, sufficiently small crystals will affect the shape and intensity of peaks, leading to significant peak broadening.

Representative peaks from the X-ray diffraction pattern of calcined SSZ-54 are shown in FIG. 1. Calcination can also result in changes in the intensities of the peaks as compared to patterns of the "as-made" material, as well as minor shifts in the diffraction pattern. The zeolite produced by exchanging the metal or other cations present in the zeolite with various other cations (such as $H^+$ or $NH_4^+$) yields essentially the same diffraction pattern, although again, there may be minor shifts in the interplanar spacing and variations in the relative intensities of the peaks. Notwithstanding these minor perturbations, the basic crystal lattice remains unchanged by these treatments.

Crystalline SSZ-54 can be used as-synthesized, but preferably will be thermally treated (calcined). Usually, it is desirable to remove the alkali metal cation by ion exchange and replace it with hydrogen, ammonium, or any desired metal ion. The zeolite can be leached with chelating agents, e.g., EDTA or dilute acid solutions, to increase the silica to alumina mole ratio. The zeolite can also be steamed; steaming helps stabilize the crystalline lattice to attack from acids.

The zeolite can be used in intimate combination with hydrogenating components, such as tungsten, vanadium, molybdenum, rhenium, nickel, cobalt, chromium, manganese or a noble metal, such as palladium or platinum, for those applications in which a hydrogenation-dehydrogenation function is desired.

Metals may also be introduced into the zeolite by replacing some of the cations in the zeolite with metal cations via standard ion exchange techniques (see, for example, U.S. Pat. Nos. 3,140,249 issued Jul. 7, 1964 to Plank et al.; 3,140,251 issued Jul. 7, 1964 to Plank et al.; and 3,140,253 issued Jul. 7, 1964 to Plank et al.). Typical replacing cations can include metal cations, e.g., rare earth, Group IA, Group IIA and Group VIII metals, as well as their mixtures. Of the replacing metallic cations, cations of metals such as rare earth, Mn, Ca, Mg, Zn, Cd, Pt, Pd, Ni, Co, Ti, Al, Sn and Fe are particularly preferred.

The hydrogen, ammonium and metal components can be ion-exchanged into the SSZ-54. The zeolite can also be impregnated with the metals, or the metals can be physically and intimately admixed with the zeolite using standard methods known to the art.

Typical ion-exchange techniques involve contacting the zeolite with a solution containing a salt of the desired replacing cation or cations. Although a wide variety of salts can be employed, chlorides and other halides, acetates, nitrates and sulfates are particularly preferred. The zeolite is usually calcined prior to the ion-exchange procedure to remove the organic matter in the channels and on the surface, since this results in a more effective ion exchange. Representative ion exchange techniques are disclosed in a wide variety of patents including U.S. Pat. Nos. 3,140,249 issued Jul. 7, 1964 to Plank et al.; 3,140,251 issued Jul. 7, 1964 to Plank et al. and 3,140,253 issued on Jul. 7, 1964 to Plank et al.

Following contact with the salt solution of the desired replacing cation, the zeolite is typically washed with water and dried at temperatures ranging from 65° C. to about 200° C. After washing, the zeolite can be calcined in air or inert gas at temperatures ranging from about 200° C. to about 800° C. for periods of time ranging from 1 to 48 hours, or more, to produce a catalytically active product especially useful in hydrocarbon conversion processes.

Regardless of the cations present in the synthesized form of SSZ-54, the special arrangement of the atoms which form the basic crystal lattice of the zeolite remains essentially unchanged.

SSZ-54 can be formed into a wide variety of physical shapes. Generally speaking, the zeolite can be in the form of a powder, a granule or a molded product, such as extrudate having a particle size sufficient to pass through a 2-mesh (Tyler) screen and be retained on a 400-mesh (Tyler) screen. In cases where the catalyst is molded, such as by extrusion with an organic binder, the zeolite can be extruded before drying, or dried or partially dried and then extruded.

SSZ-54 can be composited with other materials resistant to the temperatures and other conditions employed in organic conversion processes. Such matrix materials include active and inactive materials and synthetic or naturally occurring zeolites as well as inorganic materials such as clays, silica and metal oxides. Examples of such materials and the manner in which they can be used are disclosed in U.S. Pat. No. 4,910,006, issued May 20, 1990 to Zones et al. and U.S. Pat. No. 5,316,753, issued May 31, 1994 to Nakagawa, both of which are incorporated by reference herein in their entirety.

Hydrocarbon Conversion Processes

SSZ-54 zeolites are useful in hydrocarbon conversion reactions. Hydrocarbon conversion reactions are chemical and catalytic processes in which carbon-containing compounds are changed to different carbon-containing compounds. Examples of hydrocarbon conversion reactions in which SSZ-54 zeolites are expected to be useful include hydrocracking, catalytic cracking and olefin and aromatics formation reactions. The catalysts are also expected to be useful in other petroleum refining and hydrocarbon conversion reactions such as isomerizing n-paraffins and naphthenes, polymerizing and oligomerizing olefinic or acetylenic compounds such as isobutylene and butene-1, reforming, isomerizing polyalkyl substituted aromatics (e.g., m-xylene), and disproportionating aromatics (e.g., toluene) to provide mixtures of benzene, xylenes and higher methylbenzenes and oxidation reactions. Also included are rearrangement reactions to make various naphthalene derivatives, and forming higher molecular weight hydrocarbons from lower molecular weight hydrocarbons (e.g., methane upgrading). The SSZ-54 catalysts may have high selectivity, and under hydrocarbon conversion conditions can provide a high percentage of desired products relative to total products.

SSZ-54 zeolites can be used in processing hydrocarbonaceous feedstocks. Hydrocarbonaceous feedstocks contain carbon compounds and can be from many different sources, such as virgin petroleum fractions, recycle petroleum fractions, shale oil, liquefied coal, tar sand oil, synthetic paraffins from NAO, recycled plastic feedstocks and, in general, can be any carbon containing feedstock susceptible to zeolitic catalytic reactions. Depending on the type of processing the hydrocarbonaceous feed is to undergo, the feed can contain metal or be free of metals, it can also have high or low nitrogen or sulfur impurities. It can be appreciated, however, that in general processing will be more efficient (and the catalyst more active) the lower the metal, nitrogen, and sulfur content of the feedstock.

The conversion of hydrocarbonaceous feeds can take place in any convenient mode, for example, in fluidized bed, moving bed, or fixed bed reactors depending on the types of process desired. The formulation of the catalyst particles will vary depending on the conversion process and method of operation.

Other reactions which can be performed using the catalyst of this invention containing a metal, e.g., a Group VIII metal such platinum, include hydrogenation-dehydrogenation reactions, denitrogenation and desulfurization reactions.

The following table indicates typical reaction conditions which may be employed when using catalysts comprising SSZ-54 in the hydrocarbon conversion reactions of this invention. Preferred conditions are indicated in parentheses.

| Process | Temp.,° C. | Pressure | LHSV |
|---|---|---|---|
| Hydrocracking | 175–485 | 0.5–350 bar | 0.1–30 |
| Aromatics formation | 400–600 (480–550) | atm.–10 bar | 0.1–15 |
| Cat. cracking | 127–885 | subatm.–$^1$ (atm.–5 atm.) | 0.5–50 |
| Oligomerization | 232–649$^2$ 10–232$^4$ (27–204)$^4$ | 0.1–50 atm. — — | 0.2–50$^2$ 0.05–20$^5$ (0.1–10)$^5$ |
| Paraffins to aromatics | 100–700 | 0–1000 psig | 0.5–40$^5$ |
| Condensation of alcohols | 260–538 | 0.5–1000 psig | 0.5–50$^5$ |
| Isomerization | 93–538 (204–315) | 50–1000 psig | 1–10 (1–4) |
| Xylene isomerization | 260–593$^2$ (315–566)$^2$ 38–371$^4$ | 0.5–50 atm.$^2$ (1–5 atm)$^2$ 1–200 atm.$^4$ | 0.1–100$^5$ (0.5–50)$^5$ 0.5–50 |

| -continued | | | |
|---|---|---|---|
| Process | Temp.,° C. | Pressure | LHSV |

$^1$Several hundred atmospheres
$^2$Gas phase reaction
$^3$Hydrocarbon partial pressure
$^4$Liquid phase reaction
$^5$WHSV Other reaction conditions and parameters are provided below.

Hydrocracking

Using a catalyst which comprises SSZ-54, preferably predominantly in the hydrogen form, and a hydrogenation promoter, heavy petroleum residual feedstocks, cyclic stocks and other hydrocrackate charge stocks can be hydrocracked using the process conditions and catalyst components disclosed in the aforementioned U.S. Pat. Nos. 4,910,006 and U.S. Pat. No. 5,316,753.

The hydrocracking catalysts contain an effective amount of at least one hydrogenation component of the type commonly employed in hydrocracking catalysts. The hydrogenation component is generally selected from the group of hydrogenation catalysts consisting of one or more metals of Group VIB and Group VIII, including the salts, complexes and solutions containing such. The hydrogenation catalyst is preferably selected from the group of metals, salts and complexes thereof of the group consisting of at least one of platinum, palladium, rhodium, iridium, ruthenium and mixtures thereof or the group consisting of at least one of nickel, molybdenum, cobalt, tungsten, titanium, chromium and mixtures thereof. Reference to the catalytically active metal or metals is intended to encompass such metal or metals in the elemental state or in some form such as an oxide, sulfide, halide, carboxylate and the like. The hydrogenation catalyst is present in an effective amount to provide the hydrogenation function of the hydrocracking catalyst, and preferably in the range of from 0.05 to 25% by weight.

Aromatics Formation

SSZ-54 can be used to convert light straight run naphthas and similar mixtures to highly aromatic mixtures. Thus, normal and slightly branched chained hydrocarbons, preferably having a boiling range above about 40° C. and less than about 200° C., can be converted to products having a substantial higher octane aromatics content by contacting the hydrocarbon feed with a catalyst comprising SSZ-54. It is also possible to convert heavier feeds into BTX or naphthalene derivatives of value using a catalyst comprising SSZ-54.

The conversion catalyst preferably contains a Group VIII metal compound to have sufficient activity for commercial use. By Group VIII metal compound as used herein is meant the metal itself or a compound thereof. The Group VIII noble metals and their compounds, platinum, palladium, and iridium, or combinations thereof can be used. Rhenium or tin or a mixture thereof may also be used in conjunction with the Group VIII metal compound and preferably a noble metal compound. The most preferred metal is platinum. The amount of Group VIII metal present in the conversion catalyst should be within the normal range of use in reforming catalysts, from about 0.05 to 2.0 weight percent, preferably 0.2 to 0.8 weight percent.

It is critical to the selective production of aromatics in useful quantities that the conversion catalyst be substantially free of acidity, for example, by neutralizing the zeolite with a basic metal, e.g., alkali metal, compound. Methods for rendering the catalyst free of acidity are known in the art. See the aforementioned U.S. Pat. Nos. 4,910,006 and U.S. Pat. No. 5,316,753 for a description of such methods.

The preferred alkali metals are sodium, potassium, rubidium and cesium. The zeolite itself can be substantially free of acidity only at very high silica:alumina mole ratios.

Catalytic Cracking

Hydrocarbon cracking stocks can be catalytically cracked in the absence of hydrogen using SSZ-54, preferably predominantly in the hydrogen form.

When SSZ-54 is used as a catalytic cracking catalyst in the absence of hydrogen, the catalyst may be employed in conjunction with traditional cracking catalysts, e.g., any aluminosilicate heretofore employed as a component in cracking catalysts. Typically, these are large pore, crystalline aluminosilicates. Examples of these traditional cracking catalysts are disclosed in the aforementioned U.S. Pat. Nos. 4,910,006 and 5,316,753. When a traditional cracking catalyst (TC) component is employed, the relative weight ratio of the TC to the SSZ-54 is generally between about 1:10 and about 500:1, desirably between about 1:10 and about 200:1, preferably between about 1:2 and about 50:1, and most preferably is between about 1:1 and about 20:1. The novel zeolite and/or the traditional cracking component may be further ion exchanged with rare earth ions to modify selectivity.

The cracking catalysts are typically employed with an inorganic oxide matrix component. See the aforementioned U.S. Pat. Nos. 4,910,006 and 5,316,753 for examples of such matrix components.

Isomerization

The present catalyst can be useful for isomerizing $C_4$ to $C_7$ hydrocarbons. The activity means that the catalyst can operate at relatively low temperature which thermodynamically favors highly branched paraffins. Consequently, the catalyst can produce a high octane product. The high selectivity means that a relatively high liquid yield can be achieved when the catalyst is run at a high octane.

The present process comprises contacting the isomerization catalyst, i.e., a catalyst comprising SSZ-54 in the hydrogen form, with a hydrocarbon feed under isomerization conditions. The feed is preferably a light straight run fraction, boiling within the range of 30° F. to 250° F. and preferably from 60° F to 200° F. Preferably, the hydrocarbon feed for the process comprises a substantial amount of $C_4$ to $C_7$ normal and slightly branched low octane hydrocarbons, more preferably $C_5$ and $C_6$ hydrocarbons.

It is preferable to carry out the isomerization reaction in the presence of hydrogen. Preferably, hydrogen is added to give a hydrogen to hydrocarbon ratio ($H_2$/HC) of between 0.5 and 10 $H_2$/HC, more preferably between 1 and 8 $H_2$/HC. See the aforementioned U.S. Pat. Nos. 4,910,006 and 5,316, 753 for a further discussion of isomerization process conditions.

A low sulfur feed is especially preferred in the present process. The feed preferably contains less than 10 ppm, more preferably less than 1 ppm, and most preferably less than 0.1 ppm sulfur. In the case of a feed which is not already low in sulfur, acceptable levels can be reached by hydrogenating the feed in a presaturation zone with a hydrogenating catalyst which is resistant to sulfur poisoning. See the aforementioned U.S. Pat. Nos. 4,910,006 and 5,316,753 for a further discussion of this hydrodesulfurization process.

It is preferable to limit the nitrogen level and the water content of the feed. Catalysts and processes which are suitable for these purposes are known to those skilled in the art.

After a period of operation, the catalyst can become deactivated by sulfur or coke. See the aforementioned U.S. Pat. Nos. 4,910,006 and 5,316,753 for a further discussion of methods of removing this sulfur and coke, and of regenerating the catalyst.

The conversion catalyst preferably contains a Group VIII metal compound to have sufficient activity for commercial use. By Group VIII metal compound as used herein is meant the metal itself or a compound thereof. The Group VIII noble metals and their compounds, platinum, palladium, and iridium, or combinations thereof can be used. Rhenium and tin may also be used in conjunction with the noble metal. The most preferred metal is platinum. The amount of Group VIII metal present in the conversion catalyst should be within the normal range of use in isomerizing catalysts, from about 0.05 to 2.0 weight percent, preferably 0.2 to 0.8 weight percent.

Alkylation and Transalkylation

SSZ-54 can be used in a process for the alkylation or transalkylation of an aromatic hydrocarbon. The process comprises contacting the aromatic hydrocarbon with a $C_2$ to $C_{16}$ olefin alkylating agent or a polyalkyl aromatic hydrocarbon transalkylating agent, under at least partial liquid phase conditions, and in the presence of a catalyst comprising SSZ-54.

SSZ-54 can also be used for removing benzene from gasoline by alkylating the benzene as described above and removing the alkylated product from the gasoline.

For high catalytic activity, the SSZ-54 zeolite should be predominantly in its hydrogen ion form. It is preferred that, after calcination, at least 80% of the cation sites are occupied by hydrogen ions and/or rare earth ions.

Examples of suitable aromatic hydrocarbon feedstocks which may be alkylated or transalkylated by the process of the invention include aromatic compounds such as benzene, toluene and xylene. The preferred aromatic hydrocarbon is benzene. There may be occasions where naphthalene or naphthalene derivatives such as dimethylnaphthalene may be desirable. Mixtures of aromatic hydrocarbons may also be employed.

Suitable olefins for the alkylation of the aromatic hydrocarbon are those containing 2 to 20, preferably 2 to 4, carbon atoms, such as ethylene, propylene, butene-1, trans-butene-2 and cis-butene-2, or mixtures thereof. There may be instances where pentenes are desirable. The preferred olefins are ethylene and propylene. Longer chain alpha olefins may be used as well.

When transalkylation is desired, the transalkylating agent is a polyalkyl aromatic hydrocarbon containing two or more alkyl groups that each may have from 2 to about 4 carbon atoms. For example, suitable polyalkyl aromatic hydrocarbons include di-, tri- and tetra-alkyl aromatic hydrocarbons, such as diethylbenzene, triethylbenzene, diethylmethylbenzene (diethyltoluene), di-isopropylbenzene, di-isopropyltoluene, dibutylbenzene, and the like. Preferred polyalkyl aromatic hydrocarbons are the dialkyl benzenes. A particularly preferred polyalkyl aromatic hydrocarbon is di-isopropylbenzene.

When alkylation is the process conducted, reaction conditions are as follows. The aromatic hydrocarbon feed should be present in stoichiometric excess. It is preferred that molar ratio of aromatics to olefins be greater than four-to-one to prevent rapid catalyst fouling. The reaction temperature may range from 100° F. to 600° F., preferably 250° F. to 450° F. The reaction pressure should be sufficient to maintain at least a partial liquid phase in order to retard catalyst fouling. This is typically 50 psig to 1000 psig depending on the feedstock and reaction temperature. Contact time may range from 10 seconds to 10 hours, but is usually from 5 minutes to an hour. The weight hourly space velocity (WHSV), in terms of grams (pounds) of aromatic hydrocarbon and olefin per gram (pound) of catalyst per hour, is generally within the range of about 0.5 to 50.

When transalkylation is the process conducted, the molar ratio of aromatic hydrocarbon will generally range from about 1:1 to 25:1, and preferably from about 2:1 to 20:1. The reaction temperature may range from about 100° F. to 600° F., but it is preferably about 250° F. to 450° F. The reaction pressure should be sufficient to maintain at least a partial liquid phase, typically in the range of about 50 psig to 1000 psig, preferably 300 psig to 600 psig. The weight hourly space velocity will range from about 0.1 to 10. U.S. Pat. No. 5,082,990 issued on Jan. 21, 1992 to Hsieh, et al. describes such processes and is incorporated herein by reference.

Conversion of Paraffins to Aromatics

SSZ-54 can be used to convert light gas $C_2$–$C_6$ paraffins to higher molecular weight hydrocarbons including aromatic compounds. Preferably, the zeolite will contain a catalyst metal or metal oxide wherein said metal is selected from the group consisting of Groups IB, IIB, VIII and IIIA of the Periodic Table. Preferably, the metal is gallium, niobium, indium or zinc in the range of from about 0.05 to 5% by weight.

Xylene Isomerization

SSZ-54 may also be useful in a process for isomerizing one or more xylene isomers in a $C_8$ aromatic feed to obtain ortho-, meta-, and para-xylene in a ratio approaching the equilibrium value. In particular, xylene isomerization is used in conjunction with a separate process to manufacture para-xylene. For example, a portion of the para-xylene in a mixed $C_8$ aromatics stream may be recovered by crystallization and centrifugation. The mother liquor from the crystallizer is then reacted under xylene isomerization conditions to restore ortho-, meta- and para-xylenes to a near equilibrium ratio. At the same time, part of the ethylbenzene in the mother liquor is converted to xylenes or to products which are easily separated by filtration. The isomerate is blended with fresh feed and the combined stream is distilled to remove heavy and light by-products. The resultant $C_8$ aromatics stream is then sent to the crystallizer to repeat the cycle.

Optionally, isomerization in the vapor phase is conducted in the presence of 3.0 to 30.0 moles of hydrogen per mole of alkylbenzene (e.g., ethylbenzene). If hydrogen is used, the catalyst should comprise about 0.1 to 2.0 wt. % of a hydrogenation/dehydrogenation component selected from Group VIII (of the Periodic Table) metal component, especially platinum or nickel. By Group VIII metal component is meant the metals and their compounds such as oxides and sulfides. Optionally, the isomerization feed may contain 10 to 90 wt. % of a diluent such as toluene, trimethylbenzene, naphthenes or paraffins.

Oligomerization

It is expected that SSZ-54 can also be used to oligomerize straight and branched chain olefins having from about 2 to 21 and preferably 2–5 carbon atoms. The oligomers which are the products of the process are medium to heavy olefins which are useful for both fuels, i.e., gasoline or a gasoline blending stock and chemicals.

The oligomerization process comprises contacting the olefin feedstock in the gaseous or liquid phase with a catalyst comprising SSZ-54.

The zeolite can have the original cations associated therewith replaced by a wide variety of other cations according to techniques well known in the art. Typical cations would include hydrogen, ammonium and metal cations including mixtures of the same. Of the replacing metallic cations, particular preference is given to cations of metals such as rare earth metals, manganese, calcium, as well as metals of Group II of the Periodic Table, e.g., zinc, and Group VIII of the Periodic Table, e.g., nickel. One of the prime requisites is that the zeolite have a fairly low aromatization activity, i.e., in which the amount of aromatics produced is not more than about 20% by weight. This is accomplished by using a zeolite with controlled acid activity [alpha value] of from about 0.1 to about 120, preferably from about 0.1 to about 100, as measured by its ability to crack n-hexane.

Alpha values are defined by a standard test known in the art, e.g., as shown in U.S. Pat. No. 3,960,978 issued on Jun. 1, 1976 to Givens et al. which is incorporated totally herein by reference. If required, such zeolites may be obtained by steaming, by use in a conversion process or by any other method which may occur to one skilled in this art.

Condensation of Alcohols

SSZ-54 can be used to condense lower aliphatic alcohols having 1 to 10 carbon atoms to a gasoline boiling point hydrocarbon product comprising mixed aliphatic and aromatic hydrocarbon. The process disclosed in U.S. Pat. No. 3,894,107, issued Jul. 8, 1975 to Butter et al., describes the process conditions used in this process, which patent is incorporated totally herein by reference.

The catalyst may be in the hydrogen form or may be base exchanged or impregnated to contain ammonium or a metal cation complement, preferably in the range of from about 0.05 to 5% by weight. The metal cations that may be present include any of the metals of the Groups I through VIII of the Periodic Table. However, in the case of Group IA metals, the cation content should in no case be so large as to effectively inactivate the catalyst, nor should the exchange be such as to eliminate all acidity. There may be other processes involving treatment of oxygenated substrates where a basic catalyst is desired.

Methane Upgrading

Higher molecular weight hydrocarbons can be formed from lower molecular weight hydrocarbons by contacting the lower molecular weight hydrocarbon with a catalyst comprising SSZ-54 and a metal or metal compound capable of converting the lower molecular weight hydrocarbon to a higher molecular weight hydrocarbon. Examples of such reactions include the conversion of methane to $C_{2+}$ hydrocarbons such as ethylene or benzene or both. Examples of useful metals and metal compounds include lanthanide and or actinide metals or metal compounds.

These reactions, the metals or metal compounds employed and the conditions under which they can be run are disclosed in U.S. Pat. No. 4,734,537, issued Mar. 29, 1988 to Devries et al.; U.S. Pat. No. 4,939,311, issued Jul. 3, 1990 to Washecheck et al.; U.S. Pat. No. 4,962,261, issued Oct. 9, 1990 to Abrevaya et al.; U.S. Pat. No. 5,095,161, issued Mar. 10, 1992 to Abrevaya et al.; U.S. Pat. No. 5,105,044, issued Apr. 14, 1992 to Han et al.; U.S. Pat. No. 5,105,046, issued Apr. 14, 1992 to Washecheck; U.S. Pat. No. 5,238,898, issued Aug. 24, 1993 to Han et al.; U.S. Pat. No. 5,321,185, issued Jun. 14, 1994 to van der Vaart; and U.S. Pat. No. 5,336,825, issued Aug. 9, 1994 to Choudhary et al., each of which is incorporated herein by reference in its entirety.

EXAMPLES

The following examples demonstrate but do not limit the present invention.

Example 1

Preparation of SSZ-54

Into the Teflon cup of a Parr 23 ml reactor is placed 2 ml of a 1N KOH solution, 4 grams of water and 0.30 grams of N-isopropyl ethylenediamine. The resulting mixture is mixed by hand. 1.27 Grams of Ludox AS-30 colloidal silica (30% $SiO_2$) is added and then 0.90 gram of Nalco 1056 colloidal silica particles coated with $Al_2O_3$ is added last. The resulting reaction mixture has a silica/alumina mole ratio ("SAR") of 30. The reactor is sealed and heated at 170° C. with 43 RPM tumbling for four weeks. Analysis by XRD shows the product to be SSZ-54.

Example 2

Preparation of SSZ-54

A reaction is carried out as described in Example 1 except that the SAR is adjusted to 40 by using 1.47 grams Ludox AS-30 colloidal silica and 0.62 gram Nalco 1056 colloidal silica. A product is produced after two weeks and identified by XRD as SSZ-54.

Example 3

Preparation of SSZ-54

A reaction is carried out as described in Example 1 except that the SAR is adjusted to 50 by using 1.57 grams Ludox AS-30 colloidal silica and 0.52 gram Nalco 1056 colloidal silica. A product is produced after three weeks and identified by XRD as mostly SSZ-54 with a minor amount of cristobalite.

Example 4

Preparation of SSZ-54

0.088 Gram of Reheis F-200 dried aluminum hydroxide gel (50–53 wt. % $Al_2O_3$) is dissolved in 3 ml of a 1N KOH solution, 8.4 grams water and 0.40 gram N-isopropyl ethylenediamine. 0.90 Gram of Cabosil M5 fumed silica is blended into the resulting reaction mixture and the reactor is closed, sealed and heated at 170° C. with 45 RPM tumbling. At nine days of run time, the reaction mixture is cooled and the product is collected and washed. XRD analysis shows the product to be SSZ-54. The product had a SAR of 36.

Example 5

Preparation of SSZ-54

In the Teflon cup of a Parr 23 ml reactor, 3 grams of 1 N KOH solution, 5 grams of water and 1.90 grams of Ludox AS-30 colloidal silica are mixed. Then 0.07 gram (0.5 millimole) of 1-N-isopropyldiethylenetriamine is added to the cup. Next, 1.30 grams of Nalco 1056 colloidal silica (26 wt. % silica coated with 4 wt. % alumina) is added with spatula stirring. 0.22 Grams of isobutylamine is added and the reactor is closed and heated at 170° C. with 43 rpm tumbling. After six days, a sample is taken for scanning electron microscopy. A crystalline material is recovered and found by XRD to be SSZ-54.

Examples 6–9

Reactions are run in a manner similar to that described in Example 1 using the reagents shown in the table below. Amounts of reagents are in grams; the seeds are previously made SSZ-54. The product of each reaction is also shown in the table.

| Ex. No. | 1N KOH | Reheis F-2000 | Q[a] | Nyacol[b] | $H_2O$ | Seeds | Rxn. mix. SAR | Product |
|---|---|---|---|---|---|---|---|---|
| 6 | 3.0 | 0.10 | 0.40 | 2.25 | 5.0 | 0.05 | 30 | SSZ-54 |
| 7 | 3.0 | 0.08 | 0.40 | 2.25 | 5.0 | 0.05 | 37 | SSZ-54 |
| 8 | 3.0 | 0.06 | 0.40 | 2.25 | 5.0 | 0.05 | 50 | SSZ-54 |
| 9 | 3.0 | 0.02 | 0.40 | 2.25 | 5.0 | 0.05 | 150 | Cristobalite + Minor SSZ-54 |

[a]N-isopropyl ethylenediamine
[b]colloidal silica (40% $SiO_2$)

Example 10

Calcination of SSZ-54

The material from Example 1 is calcined in the following manner. A thin bed of material is heated in a muffle furnace from room temperature to 120° C. at a rate of 1° C. per minute and held at 120° C. for three hours. The temperature is then ramped up to 540° C. at the same rate and held at this temperature for 5 hours, after which it is increased to 594° C. and held there for another 5 hours. A 50/50 mixture of air and nitrogen is passed over the zeolite at a rate of 20 standard cubic feet per minute during heating.

Example 11

$NH_4$ Exchange

Ion exchange of calcined SSZ-54 material (prepared in Example 10) is performed using $NH_4NO_3$ to convert the zeolite from its $Na^+$ form to the $NH_4^+$ form, and, ultimately, the $H^+$ form. Typically, the same mass of $NH_4NO_3$ as zeolite is slurried in water at a ratio of 25–50:1 water to zeolite. The exchange solution is heated at 95° C. for 2 hours and then filtered. This procedure can be repeated up to three times. Following the final exchange, the zeolite is washed several times with water and dried. This $NH_4^+$ form of SSZ-54 can then be converted to the $H^+$ form by calcination (as described in Example 9) to 540° C.

Example 12

Constraint Index Determination

The hydrogen form of the zeolite of Example 11 is pelletized at 2–3 KPSI, crushed and meshed to 20–40, and then >0.50 gram is calcined at about 540° C. in air for four hours and cooled in a desiccator. 0.50 Gram is packed into a ⅜ inch stainless steel tube with alundum on both sides of the zeolite bed. A Lindburg furnace is used to heat the reactor tube. Helium is introduced into the reactor tube at 10 cc/min. and at atmospheric pressure. The reactor is heated to about 800° F., and a 50/50 (w/w) feed of n-hexane and 3-methylpentane is introduced into the reactor at a rate of 8 μl/min. Feed delivery is made via a Brownlee pump. Direct sampling into a gas chromatograph begins after 10 minutes of feed introduction. The Constraint Index value is calculated from the gas chromatographic data using methods known in the art, and is found to be 21. At 800° F. and 40 minutes on-stream, feed conversion was 40%.

What is claimed is:

1. A process for converting hydrocarbons comprising contacting a hydrocarbonaceous feed at hydrocarbon converting conditions with a catalyst comprising a zeolite having a mole ratio greater than about 20 of an oxide of a first tetravalent element to an oxide of a second tetravalent element which is different from said first tetravalent element, trivalent element, pentavalent element or mixture thereof and having, after calcination, the X-ray diffraction pattern of FIG. 1.

2. The process of claim 1 wherein the zeolite is predominantly in the hydrogen form.

3. The process of claim 1 wherein the zeolite is substantially free of acidity.

4. The process of claim 1 wherein the process is a hydrocracking process comprising contacting the catalyst with a hydrocarbon feedstock under hydrocracking conditions.

5. The process of claim 4 wherein the zeolite is predominantly in the hydrogen form.

6. The process of claim 1 wherein the process is a process for increasing the octane of a hydrocarbon feedstock to produce a product having an increased aromatics content comprising contacting a hydrocarbonaceous feedstock which comprises normal and slightly branched hydrocarbons having a boiling range above about 40° C. and less than about 200° C. under aromatic conversion conditions with the catalyst.

7. The process of claim 6 wherein the zeolite is substantially free of acid.

8. The process of claim 6 wherein the zeolite contains a Group VIII metal component.

9. The process of claim 1 wherein the process is a catalytic cracking process comprising contacting a hydrocarbon feedstock in a reaction zone under catalytic cracking conditions in the absence of added hydrogen with the catalyst.

10. The process of claim 9 wherein the zeolite is predominantly in the hydrogen form.

11. The process of claim 9 wherein the catalyst additionally comprises a large pore crystalline cracking component.

12. The process of claim 1 wherein the process is an isomerization process for isomerizing $C_4$ to $C_7$ hydrocarbons, comprising contacting a feed having normal and slightly branched $C_4$ to $C_7$ hydrocarbons under isomerizing conditions with the catalyst.

13. The process of claim 12 wherein the zeolite is predominantly in the hydrogen form.

14. The process of claim 12 wherein the zeolite has been impregnated with at least one Group VIII metal.

15. The process of claim 12 wherein the catalyst has been calcined in a steam/air mixture at an elevated temperature after impregnation of the Group VIII metal.

16. The process of claim 14 wherein the Group VIII metal is platinum.

17. The process of claim 1 wherein the process is a process for alkylating an aromatic hydrocarbon which comprises contacting under alkylation conditions at least a molar excess of an aromatic hydrocarbon with a $C_2$ to $C_{20}$ olefin under at least partial liquid phase conditions and in the presence of the catalyst.

18. The process of claim 17 wherein the zeolite is predominantly in the hydrogen form.

19. The process of claim 17 wherein the olefin is a $C_2$ to $C_4$ olefin.

20. The process of claim 19 wherein the aromatic hydrocarbon and olefin are present in a molar ratio of about 4:1 to about 20:1, respectively.

21. The process of claim 19 wherein the aromatic hydrocarbon is selected from the group consisting of benzene, toluene, ethylbenzene, xylene, naphthalene, naphthalene derivatives or mixtures thereof.

22. The process of claim 1 wherein the process is a process for transalkylating an aromatic hydrocarbon which comprises contacting under transalkylating conditions an aromatic hydrocarbon with a polyalkyl aromatic hydrocarbon under at least partial liquid phase conditions and in the presence of the catalyst.

23. The process of claim 22 wherein the zeolite is predominantly in the hydrogen form.

24. The process of claim 22 wherein the aromatic hydrocarbon and the polyalkyl aromatic hydrocarbon are present in a molar ratio of from about 1:1 to about 25:1, respectively.

25. The process of claim 22 wherein the aromatic hydrocarbon is selected from the group consisting of benzene, toluene, ethylbenzene, xylene, or mixtures thereof.

26. The process of claim 22 wherein the polyalkyl aromatic hydrocarbon is a dialkylbenzene.

27. The process of claim 1 wherein the process is a process to convert paraffins to aromatics which comprises contacting paraffins under conditions which cause paraffins to convert to aromatics with a catalyst comprising the zeolite and gallium, zinc, or a compound of gallium or zinc.

28. The process of claim 1 wherein the process is a process for isomerizing olefins comprising contacting said olefin under conditions which cause isomerization of the olefin with the catalyst.

29. The process of claim 1 wherein the process is a process for isomerizing an isomerization feed comprising an aromatic $C_8$ stream of xylene isomers or mixtures of xylene isomers and ethylbenzene, wherein a more nearly equilibrium ratio of ortho-, meta and para-xylenes is obtained, said process comprising contacting said feed under isomerization conditions with the catalyst.

30. The process of claim 1 wherein the process is a process for oligomerizing olefins comprising contacting an olefin feed under oligomerization conditions with the catalyst.

31. The process of claim 1 wherein the process is a process for the production of higher molecular weight hydrocarbons from lower molecular weight hydrocarbons comprising the steps of:

(a) introducing into a reaction zone a lower molecular weight hydrocarbon-containing gas and contacting said gas in said zone under $C_{2+}$ hydrocarbon synthesis conditions with the catalyst and a metal or metal compound capable of converting the lower molecular weight hydrocarbon to a higher molecular weight hydrocarbon; and (b) withdrawing from said reaction zone a higher molecular weight hydrocarbon-containing stream.

32. The process of claim 31 wherein the metal or metal compound comprises a lanthanide or actinide metal or metal compound.

33. The process of claim 31 wherein the lower molecular weight hydrocarbon is methane.

34. A process for converting lower alcohols and other oxygenated hydrocarbons comprising contacting said lower alcohol or other oxygenated hydrocarbon under conditions to produce liquid products with a catalyst comprising a zeolite having a mole ratio greater than about 20 of an oxide of a first tetravalent element to an oxide of a second tetravalent element which is different from said first tetravalent element, trivalent element, pentavalent element or mixture thereof and having, after calcination, the X-ray diffraction pattern of FIG. 1.

* * * * *